(12) United States Patent
Suckewer

(10) Patent No.: US 10,431,952 B2
(45) Date of Patent: Oct. 1, 2019

(54) COMPACT PLASMA ULTRAINTENSE LASER

(71) Applicant: LIGHTSENSE IP LTD., Manchester (GB)

(72) Inventor: Szymon Suckewer, Princeton, NJ (US)

(73) Assignee: LIGHTSENSE IP LTD., Manchester (GB)

( * ) Notice: Subject to any disclaimer, the term of this patent is extended or adjusted under 35 U.S.C. 154(b) by 0 days.

(21) Appl. No.: 15/893,949

(22) Filed: Feb. 12, 2018

(65) Prior Publication Data
US 2018/0331489 A1 Nov. 15, 2018

Related U.S. Application Data

(60) Provisional application No. 62/504,772, filed on May 11, 2017.

(51) Int. Cl.
*H01S 3/10* (2006.01)
*H01S 3/108* (2006.01)
(Continued)

(52) U.S. Cl.
CPC .......... *H01S 3/1086* (2013.01); *A61B 18/203* (2013.01); *A61F 9/00825* (2013.01);
(Continued)

(58) Field of Classification Search
CPC ...... H01S 3/1086; H01S 3/0057; H01S 3/302; H01S 3/305; H01S 3/005; H01S 3/0071;
(Continued)

(56) References Cited

U.S. PATENT DOCUMENTS 5,272,717 A * 12/1993 Stultz .................. H01S 3/305
359/327
6,208,458 B1 3/2001 Galvanauskas et al.
(Continued)

OTHER PUBLICATIONS

Cheng, W et al., Reaching the Nonlinear Regime of Raman Amplification of Ultrashort Laser Pulses, Physical Review Letters, US, vol. 94, No. 4, doi:10.1103/PhysRevLett_94.045003, ISSN 0031-9007, Feb. 1, 2005.
(Continued)

*Primary Examiner* — Kinam Park
(74) *Attorney, Agent, or Firm* — The Dobrusin Law Firm, P.C.

(57) ABSTRACT

Method for producing ultraintense laser pulses in which Stimulated Raman Back-Scattering (SRBS) amplifies and compresses a seed pulse, as well as an inventive compact plasma device which may implement the method. SRBS may be achieved by counter-propagating the seed pulse and a pump pulse through a few millimeter-long plasma having a plasma frequency equal to the difference between the pump and the seed pulse frequencies. Dichroic mirrors may be arranged to provide two amplifying and compression passes through the plasma, allowing greater seed pulse amplification by mitigating Landau damping within the plasma that would occur in a single pass of a plasma of double the length. Alternate examples provide for 2n number of amplification and compression passes by providing n short plasma columns, where n≥2, and additional, appropriately arranged dichroic mirrors. The compact size of the device, and the ultraintense, ultrashort pulses it emits, suit the device to dermatological applications.

36 Claims, 8 Drawing Sheets

(51) Int. Cl.
*H01S 3/102* (2006.01)
*H01S 3/094* (2006.01)
*H01S 3/30* (2006.01)
*A61B 18/20* (2006.01)
*H01S 3/00* (2006.01)
*A61F 9/008* (2006.01)
*H01S 3/16* (2006.01)
*H01S 3/23* (2006.01)
*A61B 18/00* (2006.01)
*H01S 3/11* (2006.01)

(52) U.S. Cl.
CPC ...... *H01S 3/0057* (2013.01); *H01S 3/094076* (2013.01); *H01S 3/108* (2013.01); *H01S 3/1024* (2013.01); *H01S 3/10092* (2013.01); *H01S 3/30* (2013.01); *H01S 3/302* (2013.01); *H01S 3/305* (2013.01); *A61B 2018/00583* (2013.01); *A61F 9/008* (2013.01); *A61F 2009/0087* (2013.01); *H01S 3/005* (2013.01); *H01S 3/0071* (2013.01); *H01S 3/11* (2013.01); *H01S 3/1611* (2013.01); *H01S 3/1625* (2013.01); *H01S 3/1636* (2013.01); *H01S 3/1643* (2013.01); *H01S 3/2333* (2013.01); *H01S 3/2391* (2013.01)

(58) Field of Classification Search
CPC ........ H01S 3/11; H01S 3/1611; H01S 3/1625; H01S 3/1636; H01S 3/1643; H01S 3/2333; H01S 3/2391; H01S 3/10092; H01S 3/108; H01S 3/30; H01S 3/094076; H01S 3/1024

See application file for complete search history.

(56) References Cited

U.S. PATENT DOCUMENTS

| | | | |
|---|---|---|---|
| 8,187,256 B2* | 5/2012 | Smits | A61B 18/203 128/898 |
| 9,247,995 B2* | 2/2016 | Suckewer | A61B 18/203 |
| 9,351,794 B2* | 5/2016 | Szymon Suckewer | A61B 18/203 |
| 9,653,873 B1* | 5/2017 | Sobczynski | H01S 3/073 |
| 2009/0059969 A1* | 3/2009 | Huang | H01S 3/0903 372/18 |
| 2009/0174930 A1* | 7/2009 | McCahon | H01S 3/235 359/334 |
| 2009/0316746 A1* | 12/2009 | Nowak | G03F 7/70025 372/55 |

OTHER PUBLICATIONS

Ren, J et al., A compact double-pass Raman backscattering amplifier/compressor, Physics of Plasmas., US, vol. 15, No. 5, doi:101063/1.2844352, ISSN 1070-664X, May 1, 2008.

Yang, X et al., Experimental investigation of chirp pulse Raman amplification in plasma, Harnessing Relativistic Plasma Waves As Novel Radiation Sources From Terahertz to X-Rays and Beyond II, SPIE, 1000 20th St. Bellingham WA 98225-6705 USA, vol. 8075, No. 1, doi:10.1117/12.887195, May 5, 2011.

* cited by examiner

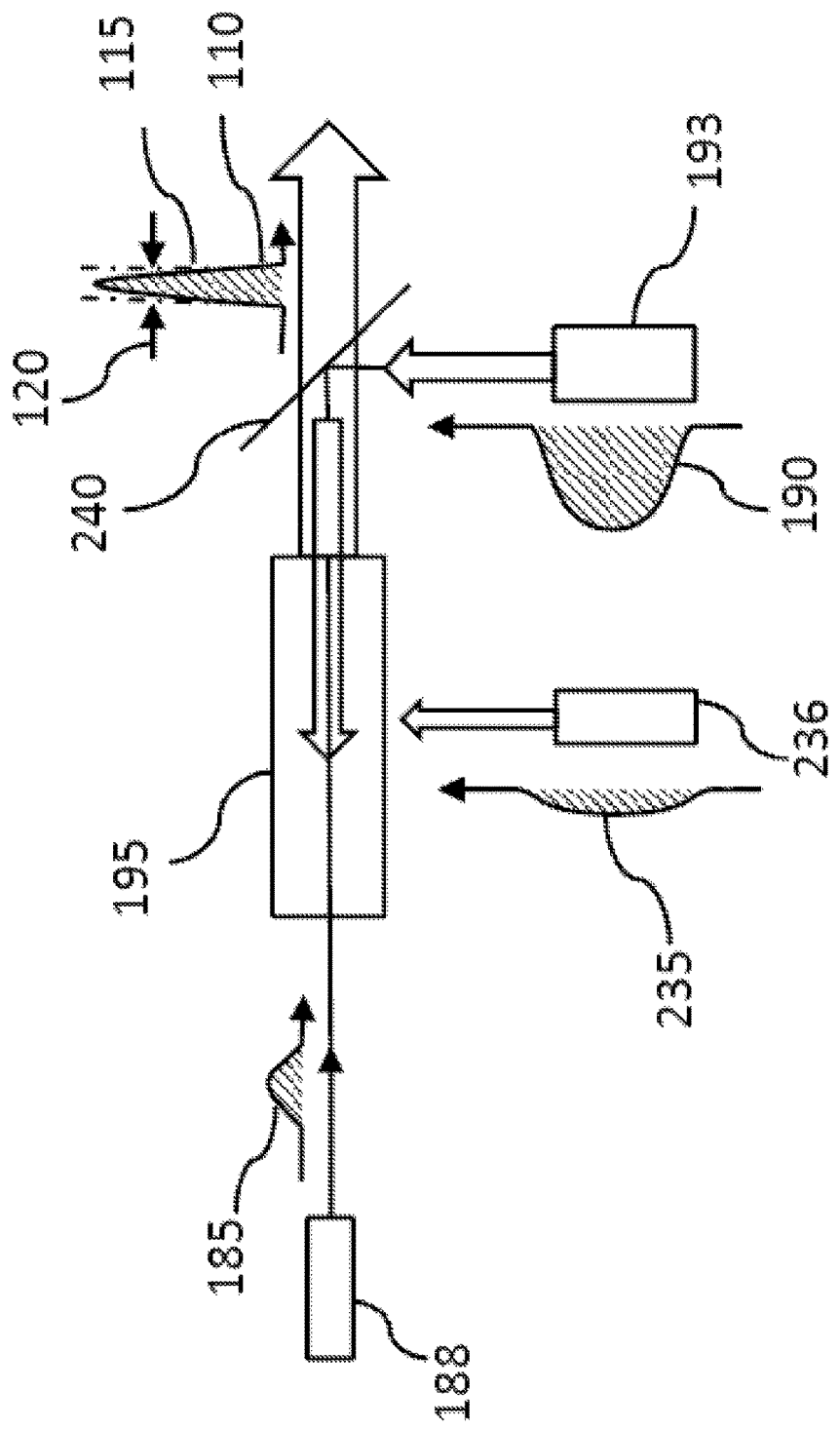

COMPACT PLASMA ULTRAINTENSE LASER

CROSS-REFERENCE TO RELATED APPLICATIONS

This application is based on, and claims priority to, U.S. Provisional Application No. 62/504,772, filed on May 11, 2017, the entire contents of which being fully incorporated herein by reference.

BACKGROUND OF THE INVENTION

1. Field of the Invention

The field of the invention relates to systems and methods for the generation of ultraintense and ultrashort laser pulses, using a compact, plasma gain and compression medium. The pulses may be useful for medical purposes, particularly for performing dermatological procedures, such as the removal of dermal tattoos, pigmented lesions, facial wrinkles, or acne scars. The pulses may be useful for ophthalmic purposes, such as cornea reshaping. The plasma gain-and-compression medium utilizes Stimulated Raman Back-Scattering (SRBS) of electromagnetic light waves to amplify and compress a "seed" pulse via a "pump" pulse that is counter-propagating in a (e.g. small) plasma column, thereby forming femtosecond laser pulses of very high intensity.

2. Technical Background

A technical problem, inherent in the field of laser physics, is that in order to produce high intensity, ultrashort laser pulses using current methods and devices, expensive, damage prone optical elements such as, but not limited to, amplifier crystals and pulse compressor gratings, are required.

A technical solution disclosed herein is to replace the most vulnerable of those expensive, damage prone optical elements with a small, inexpensive plasma column that may be used both to amplify and to temporally compress optical pulses in a broad spectral range from the ultraviolet (UV) to the infrared (IR). In this way, ultrashort pulses of very high intensity may be produced with far less regard for damage threshold limits, resulting in more affordable and more robust femtosecond type lasers.

A plasma column is a region of plasma, in a vacuum chamber, in which the plasma region is elongated in shape in one direction, when compared to directions perpendicular to the direction of elongation.

The process termed multi-photon ablation is a completely different method of material removal than photo-ablation. In multi-photon ablation, individual molecules absorb several photons almost instantaneously, in a timeframe that is faster than the molecule's or atom's relaxation time. This creates an ultra-high electric field in the vicinity of such molecules or atoms that frees them from the tissue being multi-photon ablated. Multi-photon ablation requires a very high laser pulse intensity, approximately equal to or higher than $10^{12}$ W/cm$^2$, and preferably in the range of $10^{13}$ to $10^{15}$ W/cm$^2$. This causes a non-thermal ablation of matter, whereas other laser based ablation methods are thermal.

3. Description of the Related Art

In the U.S. Pat. No. 8,187,256 issued on May 29, 2012 entitled "Tattoo removal and other dermatological treatments using multi-photon processing", the contents of which are hereby incorporated by reference in their entirety, it was shown how femtosecond lasers may be of significant use in a variety of medical applications such as, but not limited to, the treatment of various dermatological conditions including the painless, scar-less, and rapid, removal of tattoos. It was also noted how such applications may benefit significantly if the expensive femtosecond (fsec) solid state Ti:Sapphire lasers that were used to obtain the appropriately short and intense laser pulses, could be replaced by a significantly less expensive fsec-type laser. This insight stimulated our search for a new type of fsec laser, in which expensive crystals for amplification of pulses and gratings for their compression would be replaced by very inexpensive lasing media. The result was the present disclosure, the Compact Plasma Ultraintense Laser (C-PUL), and its possible application to dermatology.

As detailed in U.S. Pat. No. 8,187,256 referenced above, an advantage of a femtosecond-type laser over longer pulse duration lasers in medical applications may be that, because of the very short pulse, a relatively small amount of energy may be focused down into a small enough volume to produce a localized, and efficient, laser-tissue interaction process. This may occur because the electromagnetic field produced by so low energy pulses, but when compressed into such a small space in such a short time, may be sufficiently large as to directly disrupt the electrons of the molecule, bypassing the need to heat an entire cluster of molecules to disrupt them, as is done in more conventional laser ablation.

Furthermore, because the energy may be applied in a time that is short compared to the relaxation time of the molecule, any damage may be highly localized as there may be little excess energy, and insufficient time for it to be transferred to, and so damage, surrounding tissue.

A further advantage of high intensity femtosecond laser pulse initiated processes, applicable to tasks such as tattoo removal, may be that the disruption process acts practically independently of the spectral absorption characteristics of the targeted molecules. This, for instance, obviates the need to match the wavelength of the laser to the color of the dye being removed.

An intensity of electromagnetic radiation of $10^{12}$ W/cm$^2$ or more may be required to initiate such processes or events. This level of intensity may be achieved by focusing a pulse containing only a few mJ of energy, but having a temporal pulse length of a few hundred fsec or less, down to a focal volume having a diameter of about 20 µm.

One laser typically used to generate femtosecond pulses, is a suitably configured Titanium doped sapphire (Ti:Sapphire) solid state laser. Such a laser may be configured to be a tunable laser operating over a broad range of near infra-red wavelengths centered at 800 nm, and generate femtosecond pulses having a temporal duration in the range of 50 to 300 fsec and a preferable pulse energy of 2mJ, but which may be as low as 0.2mJ or as high as 20mJ. However, such a laser requires relatively expensive amplifier crystals, as well as costly gratings, to achieve the required laser pulse intensity without creating local intra-cavity power densities that may damage the amplifier crystals, gratings or other laser optics.

What is desirable is a significantly less expensive, more robust femtosecond laser that reliably provides the requisite high intensity pulses needed for more affordable dermatological procedures, particularly dermal tattoo removal. The pulses may also be used in ophthalmic procedures.

While conducting research on the amplification and compression of laser pulses using Stimulated Raman Back- Scattering (SRBS) in a plasma, we were able to produce output pulses of unprecedentedly high intensity. Indeed, it became apparent that it may be feasible to create a very practical, relatively inexpensive, and compact, femtosecond-type plasma laser, that may be especially useful for dermatological applications. Such a laser may provide an output beam having a power in a range of several milli-Joules (mJ) to several dozen mJ with a pulse duration at least as short as 50 to 100-femtoseconds (fsec), and may be even shorter. If necessary, longer pulses may also be produced by decreasing their compression in the plasma.

Plasmas have the ability to sustain very high laser intensities, several orders of magnitude higher than in the solid state optics presently used in ultrashort pulse lasers. Plasmas, in contrast to solid state optics, may, therefore, not be damaged by high pulse intensities. This may allow pulses to be amplified and compressed in plasmas to intra-cavity intensities that are several orders of magnitude higher than may be possible in the intra-cavity of present solid state lasers.

The ability to withstand such high intensities may also allow plasma based lasers to be significantly more compact than solid state lasers capable of producing similar, suitably short femtosecond pulses.

The relevant prior art also includes:

In U.S. Pat. No. 9,247,995 entitled "Tattoo removal with two laser beams via multi-photon processes", a method for removing tattoos using two laser beams and a multi-photon process is disclosed. A 0.1 to 100 nsec pulse secondary laser beam, focused to an intensity of $10^8$ W/cm$^2$ or higher, creates a temporary channel from the skin surface to the tattoo pigment. A 100 fsec pulse main laser beam is then guided through the channel to the pigment and focused to sufficient intensity, i.e., $10^{12}$ W/cm$^2$ or more, to initiate a process that breaks up the pigment, disrupting its light reflecting properties. The channel allows the main laser beam unobstructed passage to the pigments via a channel-waveguide, resulting in efficient use of the main laser. A suitably configured Ti/Sapphire laser beam is split into two components, with an uncompressed component used as the secondary laser beam, and a compressed component as the main laser beam.

U.S. Pat. No. 5,272,717 entitled "Single focus backward Raman laser" describes a single focus backward Raman laser that is a compact, efficient apparatus for converting light at a first wavelength provided by a pump laser to light at a Raman-shifted wavelength. The laser is comprised of a gas cell, two lenses, a feedback mirror, an optical isolator, and a dichroic mirror, and the gas cell contains a Raman gas medium. The Raman gas medium may be methane, hydrogen, or deuterium, for example. The two lenses bring the pump and Raman light to a single focus in the gas cell and also re-collimate the light after it exits the cell. The optical isolator is used to prevent the backward-scattered pump light from re-entering the pump laser. The dichroic mirror is used to reflect out the backward-scattered Raman light, while transmitting the pump laser light. The present laser has a much improved beam divergence and is much less sensitive to optical misalignments than conventional Raman half-resonator designs. The present laser is also less complex and is more compact than a multiple focus backward Raman laser, with substantially identical Raman conversion efficiency and beam divergence. The present laser may be adapted to replace the Raman half-resonator and the multiple focus backward Raman laser in high pulse repetition rate (>1 Hz), medium-energy (>100 mJ, 1.54 μm) laser designs.

Various implementations are known in the art, but fail to address all of the problems solved by aspects of the invention described herein. Various examples of aspects of this invention are illustrated in the accompanying drawings and will be described in more detail herein below.

SUMMARY OF THE INVENTION

According to a first aspect of the invention, there is provided an apparatus arranged to produce femtosecond laser pulses, the apparatus including a laser system arranged to produce nanosecond or picosecond laser pulses, an optical system configured to produce pump pulses and seed pulses from the nanosecond or picosecond laser pulses, and plasma generation apparatus including a vacuum chamber and plasma column generation apparatus arranged to generate a plasma column in the vacuum chamber, wherein the optical system is arranged to counterpropagate the pump pulses and the seed pulses along the plasma column, wherein the optical system is arranged to cause the pump pulses and the seed pulses to overlap in space and in time, in the plasma column, to amplify the seed pulses to produce amplified pulses, and to temporally shorten the amplified pulses compared to the seed pulses, to produce femtosecond amplified and shortened pulses, using stimulated Raman backscattering (SRBS) in the plasma column.

An advantage is that the apparatus may provide femtosecond pulses more inexpensively than a solid state laser system. An advantage is that the plasma column is more resistant to optical damage than comparable solid or liquid optical components. An advantage is that the gas resulting from the plasma is of a low volume, which can hence be more readily pumped out from the vacuum chamber, than for larger volume plasmas. An advantage is that the plasma may be kept well away from the walls of the vacuum chamber, or from components in the vacuum chamber, which may prevent damage to the walls of the vacuum chamber, or to components in the vacuum chamber.

The apparatus may be one wherein the femtosecond amplified and shortened pulses have a pulse energy in the range of 0.5 mJ to 200 mJ. An advantage is that such pulse energies may be used in dermatological treatment, or in ophthalmic treatment.

The apparatus may be one wherein the femtosecond amplified and shortened pulses have a pulse energy in the range of 1 mJ to 40 mJ. An advantage is that such pulse energies may be used in dermatological treatment, or in ophthalmic treatment.

The apparatus may be one wherein the femtosecond amplified and shortened pulses have a pulse energy in the range of 2 mJ to 15 mJ. An advantage is that such pulse energies may be used in dermatological treatment, or in ophthalmic treatment.

The apparatus may be one wherein the femtosecond amplified and shortened pulses have a pulse FWHM (full width half maximum) duration below 500 fs. An advantage is that such pulse durations may keep patient discomfort to a minimal level in dermatological treatment.

The apparatus may be one wherein the femtosecond amplified and shortened pulses have a pulse FWHM (full width half maximum) duration of 100 fs or less. An advantage is that such pulse durations may keep patient discomfort to a minimal level in dermatological treatment.

The apparatus may be one wherein the femtosecond amplified and shortened pulses have a pulse FWHM (full width half maximum) duration of from 30 fs to 100 fs. An advantage is that such pulse durations may keep patient discomfort to a minimal level in dermatological treatment.

The apparatus may be one wherein the plasma column is less than 3.0 cm in length, e.g. less than 1.0 cm in length. Such a relatively long plasma column can provide larger amplification of pulses, if amplification dumping of pulses in the plasma is not increasing significantly with increase of the plasma length.

The apparatus may be one wherein the plasma column is less than 3 mm in length. An advantage is that such plasma column could be of the optimal length for the fsec-type of the compact plasma laser to be used in dermatological and in ophthalmic treatments.

The apparatus may be one wherein the plasma column is less than 100 μm in diameter. An advantage is that the gas being used to create the plasma and gas resulting from the plasma is of a low volume, which can hence be more readily pumped out from the vacuum chamber, than for larger volume plasmas.

The apparatus may be one wherein the apparatus is less expensive than a Ti:sapphire laser system with equivalent laser pulse output.

The apparatus may be one wherein the optical system is arranged such that after a first pass of the plasma column, a second pass of the plasma column by the laser pulses is provided, to provide femtosecond pulses which are further amplified and further shortened pulses, by further stimulated Raman backscattering (SRBS) in the plasma column, in the second pass of the plasma column. An advantage is an efficient use of the plasma in generating femtosecond further amplified and further shortened pulses.

The apparatus may be one in which the plasma column generation apparatus is arranged to generate one or more additional plasma columns in the vacuum chamber, wherein the optical system is arranged to counterpropagate the pump pulses and the femtosecond pulses which are amplified and shortened along the one or more additional plasma columns, wherein the optical system is arranged to cause the pump pulses and the femtosecond pulses which are amplified and shortened to overlap in space and in time, in the one or more additional plasma columns, to further amplify the femtosecond pulses which are amplified and shortened to produce further amplified pulses, and to temporally shorten the further amplified pulses, to produce further amplified and shortened femtosecond pulses, using stimulated Raman backscattering (SRBS) in each of the one or more additional plasma columns. An advantage is generation of femtosecond further amplified and further shortened pulses.

The apparatus may be one wherein the plasma column generation apparatus comprises a suitable material. The apparatus may be one wherein the plasma column generation apparatus includes a laser for laser ablation, arranged to perform laser ablation of the suitable material. An advantage is that plasma column generation may be synchronized with the transmission of pump and seed pulses into the vacuum chamber. The apparatus may be one wherein the suitable material includes an open ended plastic microcapillary.

The apparatus may be one wherein the plasma column generation apparatus comprises a gas jet and a high voltage apparatus arranged to perform high voltage ionization of the gas jet. An advantage is that the plasma column may be generated in a simplified way, hence in a more robust and less expensive way.

The apparatus may be one wherein the plasma column generation apparatus includes a gas nozzle within the vacuum chamber, arranged to emit the gas jet.

The apparatus may be one wherein the gas jet is injected into a plastic microcapillary, in which the gas jet injected into the plastic microcapillary is ionized in the plastic microcapillary.

The apparatus may be one wherein the gas jet is a gas jet of Hydrogen ($H_2$), Nitrogen ($N_2$), or Ethane ($C_2H_6$), or some combination thereof.

The apparatus may be one wherein the apparatus is mobile. An advantage is that the apparatus is readily transportable within premises.

The apparatus may be one including a cart, the cart supporting the laser system, the optical system, and the plasma generation apparatus, wherein the cart is operable to transport the laser system, the optical system, and the plasma generation apparatus. An advantage is that the apparatus is readily transportable within premises.

According to a second aspect of the invention, there is provided a method of using an apparatus arranged to produce femtosecond laser pulses, the apparatus including a laser system arranged to produce nanosecond or picosecond laser pulses, an optical system configured to produce pump pulses and seed pulses from the nanosecond or picosecond laser pulses, and plasma generation apparatus including a vacuum chamber and plasma column generation apparatus arranged to generate a plasma column in the vacuum chamber, wherein the optical system is arranged to counterpropagate the pump pulses and the seed pulses along the plasma column, wherein the optical system is arranged to cause the pump pulses and the seed pulses to overlap in space and in time, in the plasma column, to amplify the seed pulses to produce amplified pulses, and to temporally shorten the amplified pulses compared to the seed pulses, to produce femtosecond amplified and shortened pulses, using stimulated Raman backscattering (SRBS) in the plasma column, the method including the step of using the apparatus for dermatological treatment, or in ophthalmic treatment. An advantage is a reduction in the cost of providing the dermatological treatment, or the ophthalmic treatment. An advantage is that because the plasma column is more resistant to optical damage than comparable solid or liquid optical components, the time and cost required for servicing the apparatus is reduced.

The method may be one wherein the dermatological treatment is non-therapeutic.

The method may be one wherein the dermatological treatment includes tattoo removal.

The method may be one wherein the dermatological treatment includes treatment of superficial vascular malformations (port-wine stains), or facial telangiectases, or rosacea related erythema/redness, or hemangiomas, or pyogenic granulomas, or Kaposi sarcoma, or poikiloderma of Civatte, or lentiginous regions, or birthmarks, or facial wrinkles, or acne scars, or sun-damaged skin.

The method may be one wherein the dermatological treatment includes use of multi-photon ablation.

According to a third aspect of the invention, there is provided a method for providing a compact laser having utltrashort and ultraintense output pulses, comprising:

providing a seed optical pulse having a seed wavelength, $\lambda_{seed}$, with a frequency $\omega_{seed}$;

providing a pump optical pulse having a pump wavelength, $\lambda_{pump}$ with a frequency $\omega_{pump}$;

providing a first plasma column having a plasma frequency, $\omega_p$, and wherein said plasma frequency, said seed frequency, and said pump frequency satisfy the condition that:

$\omega_p = \omega_{pump} - \omega_{seed}$;

propagating said seed optical pulse through said first plasma column in a first direction; and simultaneously propagating said pump optical pulse through said first plasma column in a second, opposite direction such that said counter-propagating seed optical pulse and pump optical pulse are coupled by said first plasma column to produce Stimulated Raman Back-Scattering such that said seed optical pulse is amplified, and shortened in temporal length.

The method may be one further comprising:
providing a beam splitter comprising a saturable absorber;
providing a 1st wavelength selective mirror being transmitting at said seed wavelength, $\lambda_{seed}$, and reflective at said pump wavelength, $\lambda_{pump}$ and located between said beam splitter and said plasma column;
providing a 2nd wavelength selective mirror being transmitting at said pump wavelength, $\lambda_{pump}$, and reflective at said seed wavelength, $\lambda_{seed}$ and located on an opposite side of said plasma column to said beam splitter; using said beam splitter to propagate said seed optical pulse through said 1st wavelength selective mirror and then through said plasma column, while simultaneously counter-propagating said pump optical pulse through said 2nd wavelength selective mirror and then through said plasma column; and then, reflecting said pump optical pulse from said 1st wavelength selective mirror back through said plasma column, while simultaneously reflecting said seed optical pulse from said 2nd wavelength selective mirror, through said plasma column, then through said 1st wavelength selective mirror, then through said beam splitter comprising a saturable absorber, thereby producing a twice amplified and compressed seed optical pulse as an output laser pulse.

The method may be one wherein said seed optical pulse has a seed optical pulse energy of less than 100 μJ and a seed optical pulse width of less than 1 psec; and said pump optical pulse having a pump optical pulse energy of less than 200mJ and a pump optical pulse width of less than 50 psec, and wherein said output laser pulse has a pulse width less than 300 fsec.

The method may be one wherein said plasma column has a length shorter than 5 mm.

The method may be one wherein said plasma column is one of a hydrogen plasma, an ethane plasma and a nitrogen plasma, or some combination thereof.

The method may be one wherein said plasma column is an ethane plasma.

The method may be one wherein said pump optical pulse has a wavelength of 532 nm, said seed optical pulse has a wavelength of 566.5 nm and said plasma has an electron density of $1.3 \times 10^{19}$ electrons/cm$^3$.

The method may be one including a step of using a cylindrical microcapillary tube having an internal diameter of less than 500 μm, a length less than 10 mm and an initial, internal gas pressure of less than 100 Torr and wherein said plasma column is contained within said microcapillary tube.

The method may be one such that the microcapillary tube further comprises a polyethane tube, wherein formation of said plasma column is initiated by laser ablation of said polyethane tube.

The method may be one further comprising:
a second plasma column oriented substantially parallel to said first plasma column;
a third and a fourth wavelength selective mirror being transmitting at said seed wavelength, $\lambda_{seed}$, and reflective at said pump wavelength, $\lambda_{pump}$;
a fifth and a sixth wavelength selective mirror being transmitting at said pump wavelength, $\lambda_{pump}$, and reflective at said seed wavelength, $\lambda_{seed}$, and
wherein, said six wavelength selective mirrors are positioned and oriented such that said seed optical pulse and said pump optical pulse simultaneously counter-propagate through said first plasma column, then simultaneously counter-propagate twice through said second plasma column, and then simultaneously counter-propagate through said first plasma column, thereby amplifying and compressing said seed optical pulse four times to produce said output laser pulse.

An inventive method for providing utltrashort, ultraintense laser pulses is disclosed, as well as an inventive device which may implement that method.

The output pulses provided by the inventive device may be suitable for dermatological procedures such as tattoo removal, or in ophthalmic treatment. The inventive device, which may result from the inventive method may, for instance, be used to provide an output laser pulse having a pulse energy greater than 2mJ and a pulse width less than 500 fsec. Using a suitable optical delivery system, this output laser pulse may, for instance, be focused to a focal volume small enough to provide a power density greater than $10^{12}$ Watts/cm$^2$ in a vicinity of a tattoo ink pigment particle. This level of intensity may initiate highly localized processes that may break the tattoo ink pigment particles into two or more constituent parts, with little or no damage to surrounding tissue.

In a preferred example, termed a Compact-Plasma Ultraintense Laser (C-PUL), the innovative device operates using Stimulated Raman Back-Scattering (SRBS) in an ionized gas (plasma) for both amplification and compression. A seed pulse that counter propagates with a pump pulse through the plasma may be both amplified and temporally shortened. The temporal shortening, or reduction of the pulse duration, may occur because a combination of pump pulse depletion and the non-linear nature of the amplification process may result in the trailing portion of the seed pulse not being amplified significantly.

For instance, a suitably ionized, 2 mm long, 50 μm diameter, columnar ethane plasma may be used to interact an 803 nm wavelength pump pulse, having 90mJ of energy, and a 20 psec full-width-half-maximum (FWHM) pulse duration with a counter propagating 878 nm wavelength seed pulse, initially having 16 μJ of energy and a 550 fsec FWHM pulse duration, and, by Stimulated Raman Back-Scattering amplification, produce an 878 nm output pulse having slightly less than 4mJ of energy and about 100 fsec FWHM pulse duration. As the seed pulse itself may have been originated as a first Stoke beam from an 803 nm wavelength of a Ti:Sapphire laser beam, the total intensity amplification of such a system may be about 10,000. Such an output pulse, when focused down to an appropriate focal volume may provide a pulse power density (i.e. a pulse intensity) greater than $10^{12}$ Watts/cm$^2$, which may be sufficient to initiate the highly localized processes required, for instance, for tattoo removal that may be rapid, painless, and scarless.

In a further preferred example of an aspect of the invention, the output pulse may be provided by a multi-pass, Compact Plasma Ultraintense Laser (mpC-PUL). This mpC-PUL may, for instance, be a two-pass system that may be accomplished by providing two wavelength selective mirrors. The first may selectively transmit at the seed pulse wavelength, but be reflective at the pump pulse wavelength and may be placed at the output end of the columnar plasma. The second may selectively transmit at the pump pulse wavelength and reflect at the seed pulse wavelength. In this way, the pump and seed pulses may be made to counter propagate twice through the plasma, with the seed pulse being amplified and temporally compressed on both passes. Such an arrangement may, for instance, be used to produce an output pulse being further temporally compressed to about 50 fsec, and having a peak pulse intensity amplification of 20,000.

The need for a double pass Stimulated Raman Back-Scattering laser stems from the fact that in addition to amplification, there is a competing process of Landau damping of electromagnetic (EM) waves in the plasma. This occurs as the plasma temperature increases due to the uninterrupted pump-heating of the plasma. This Landau damping process diminishes the amplification over time and distance. It is not, therefore, possible to simply double the length of the plasma column to obtain additional gain as may be done in most conventional lasing mediums. The double pass system introduces enough of a temporal delay of the pumping that the plasma may cool down, decreasing the Landau damping. A second pass through the somewhat cooled plasma may, therefore, result in further increases in amplification, and further compression, of the pulses. More complex mirror arrangements may allow for an even higher number of effective passes.

The higher amplification of the multi-pass system may mean that a less powerful, and therefore less expensive, system-driving laser may be used to obtain the same intensity of final output pulse.

Therefore, aspects of the present invention succeed in conferring the following, and others not mentioned, desirable and useful benefits and objectives.

It is an object of the work to provide a robust, inexpensive laser capable of providing very high intensity pulses of relatively low energy.

It is a further object of the present invention to provide a significantly less expensive and more powerful system than solid-state utltrashort pulse lasers of similar parameters, suitable for dermatological applications, or in ophthalmic treatment.

Femtosecond laser pulses may be defined to include laser pulses with a characteristic duration of one to 999 fsec, where 1 fsec=$10^{-15}$ sec. Picoosecond laser pulses may be defined to include laser pulses with a characteristic duration of one to 999 psec, where 1 psec=$10^{-12}$ sec. Nanosecond laser pulses may be defined to include laser pulses with a characteristic duration of one to 999 nsec, where 1 nsec=$10^{-9}$ sec.

Pulse widths referred to herein are pulse widths measured using the FWHM.

While multiphoton processes are referred to herein in the context of dermatological treatments using femtosecond laser pulses, dermatological treatments using femtosecond laser pulses may include other processes, besides multiphoton processes.

BRIEF DESCRIPTION OF THE FIGURES

Aspects of the invention will now be described, by way of example(s), with reference to the following Figures, in which:

FIG. 1A shows a schematic representation of a single-pass, Compact-Plasma Ultraintense Laser (C-PUL) of one example of an aspect of the present invention.

DETAILED DESCRIPTION

Figure 1B:
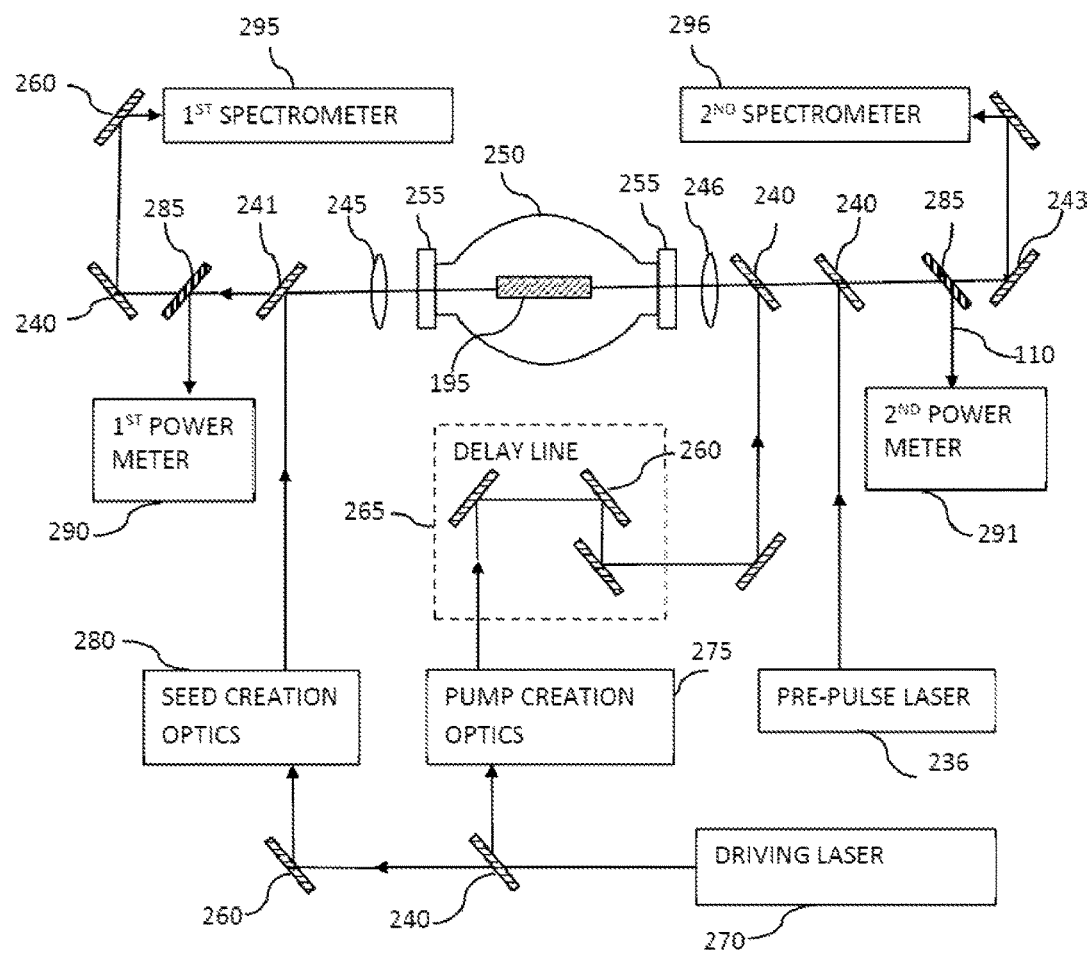
FIG. 1B shows a schematic representation of some significant components of a single-pass, Compact-Plasma Ultraintense Laser (C-PUL) of one example of an aspect of the present invention.

The preferred examples of aspects of the present invention will now be described in more detail with reference to the drawings in which identical elements in the various figures are, as far as possible, identified with the same reference numerals. These examples are provided by way of explanation of aspects of the present invention, which are not, however, intended to be limited thereto. Those of ordinary skill in the art may appreciate upon reading the present specification and viewing the present drawings that various modifications and variations may be made thereto without departing from the spirit and scope of the invention.

FIG. 1A shows a schematic representation of a single-pass, Compact-Plasma Ultraintense Laser (C-PUL) of one example of an aspect of the present invention.

The novel laser of an aspect of the present invention is based on the well-known phenomenon of Stimulated Raman Back-Scattering (SRBS) in a plasma. Using a plasma as a lasing medium has the advantages over a solid state medium in that the plasma cannot be damaged by the very high intensities of ultrashort laser pulses as they are amplified and compressed. Stimulated Raman Back-Scattering in a plasma may be particularly useful as it may allow the creation of a very practical, compact, and relatively inexpensive femtosecond-type of laser that may be of considerable commercial use in providing reasonably priced dermatological procedures such as, but not limited to, tattoo removal.

Such a plasma based Stimulated Raman Back-Scattering (SRBS) laser may, for instance, be used to produce pulses having energies in a range from 0.5mJ to 40mJ, though in a preferred example, that may be more practicable, the pulses may have energies in a range from 1mJ to 15mJ. The SRBS laser of an aspect of the present invention may also have temporal pulse lengths in a range of 100-femtoseconds down to 50-femtoseconds. If desired, pulse lengths may be increased by decreasing their compression in the plasma and, to, for instance, match the pulse energies, to be in a range of 100 picoseconds to 100 femtoseconds.

Stimulated Raman Back-Scattering in a plasma has the additional advantage that the plasma may serve both as an amplifying medium and as a pulse compression medium.

As shown schematically in FIG. 1A, the Compact-Plasma Ultraintense Laser (C-PUL) 105 may function by having a columnar plasma 195 into which a seed pulse 185 from a seed pulse laser 188 is focused. Simultaneously, a counter-propagating pump pulse 190 emanating from a pump pulse laser 193 may be brought into alignment by a wavelength selective mirror 240, or a beam splitter having a saturable absorber, and may also be focused into the plasma. The columnar plasma 195 may, for instance, be created by laser ablation of a suitable material using a pre-pulse 235 from a pre-pulse laser 236, or it may be created by high voltage ionization of a gas jet, in which case the pre-pulse 235 may also effectively create a waveguide that may facilitate the propagation of high intensity fsec pulses.

Such a system may, for instance, be used to provide an output laser pulse 110 having a pulse energy 115 greater than 2mJ and a pulse width 120 less than 100 fsec. Such a pulse, when focused down to a focal spot radius of 50 μm, may provide a pulse power density (i.e. a pulse intensity) greater than $10^{12}$ Watts/cm$^2$, which may be sufficient to initiate a highly localized process via high intensity electromagnetic (EM) waves, capable of disrupting molecules by direct interaction of EM waves with their electrons, rather than via thermal heating of the molecules.

Amplification by Stimulated Raman Back-Scattering may be considered to be the result of the three-waves interaction, or oscillating systems. A plasma has a characteristic plasma frequency that may be determined primarily by the density of the electrons in the plasma and the temperature of the electrons. This characteristic plasma frequency allows EM waves to propagate through the plasma at that frequency when, as here, the plasma frequency is much less than the pump frequency and the seed frequency; it follows that the plasma is relatively transparent at the pump frequency and at the seed frequency. If the frequency difference between the two laser pulses matches the plasma frequency, energy may be transferred from a pumping laser pulse, that may have a higher frequency, $\omega_{pump}$, to a seed pulse that may have a lower frequency, $\omega_{seed}$. This condition may be satisfied if there is a resonant condition for a process of efficient transfer of energy from the pump to the seed. This may be if $$\omega_p = \omega_{pump} - \omega_{seed} \tag{1}$$

where $\omega_p$ is the plasma frequency, $\omega_{pump}$ is the pump laser frequency and $\omega_{seed}$ is the seed laser pulse frequency.

For instance, a seed pulse having a wavelength of 878 nm and a pump pulse having a wavelength 803 nm may satisfy such a condition in a plasma having an electron density of $1.3 \times 10^{19}$ cm$^{-3}$.

FIG. 1B shows a schematic representation of some significant components of a single-pass, Compact-Plasma Ultraintense Laser (C-PUL) of one example of an aspect of the present invention.

The columnar plasma 195 that may be used as the amplifying and the compressing medium may, for instance, be formed from a jet of a gaseous form of a compound such as, but not limited to, Hydrogen ($H_2$), Ethane ($C_2H_6$), or some combination thereof. The compound, in gaseous form, may, for instance, be emitted from a gas nozzle within a vacuum chamber 250.

The gas may be ionized into a suitable plasma by a pre-pulse emanating from a pre-pulse laser 236 and directed toward the plasma via a wavelength selective mirror or beam splitter 240. The pre-pulse laser 236 may, for instance, be a Nd:YAG laser having a wavelength of 1.064 μm and emitting pulses of approximately 6 ns in duration with a pulse energy of approximately 500mJ. When focused down to a diameter of about 50 μm, such a pulse may produce an intensity of $4 \times 10^{12}$ W/cm$^2$, sufficient to ionize the gas and produce a plasma channel suitable to act as a seed pulse amplification and compression medium.

A driving laser 270 may then be used to produce both the seed and the pump pulses. The output of the driving laser 270 may, for instance, be split into two by a wavelength selective beam splitter 240. Part of the beam may then go through pump creation optics 275 before being fed onto to a delay line 265 and then via a wavelength selective mirror or beam splitter 240 to a 2nd focusing optical system 246 that may focus it through a vacuum chamber optical window 255 into the columnar plasma 195. The other part of the driving laser 270 beam may be fed via a steering mirror 260 into the seed creation optics 280 before going on to a 2nd type of wavelength selective mirror or beam splitter 241 and being focused through a vacuum chamber optical window 255 onto the columnar plasma 195 by a 1st focusing optical system 245, and so propagate through the columnar plasma 195 in the opposite direction to the pump pulse.

In a preferred example, the driving laser 270 may be a Ti:Sapphire laser system having a central wavelength of 803 nm with a bandwidth of approximately 12 nm and a pulse duration (FWHM) of approximately 240 psec. 95% of the pulse from the driving laser 270 may be sent to the pump creation optics 275 to be compressed to a pulse of approximately 20 psec having the same central wavelength of 803 nm and the same bandwidth of 12 nm. The other 5% of the driving laser 270 may be sent to a seed creation optics 280 unit that may include a Raman crystal such as, but not limited to, a 7 cm-long barium nitride Raman crystal. This Raman crystal may be used to generate the first Stoke beam, which in this instance may be a beam with a central wavelength of 878 nm and a slightly narrow bandwidth of approximately 9 nm. This first Stoke beam may then be compressed, in this instance, to an approximately 500 fsec pulse, and used as the seed pulse.

The arrangement shown in FIG. 1B may be used for the initial, or experimental, setup and testing of the system. The 1st spectrometer 295 and the 2nd spectrometer 296 as well as the 1st power meter 290 and the 2nd power meter 291 may, for instance, be useful in the initial stages of maximizing the output energy. The 2nd power meter 291 and the 2nd spectrometer 296 that may be used to monitor the output laser pulse 110 may, for instance, be useful in helping eliminate scattered signals occurring at wavelengths different from the desired wavelength.

A system of the arrangement shown in FIG. 1B may, for instance, be used in the following manner. A suitably ionized, 2 mm long, 50 μm diameter, columnar ethane plasma may, for instance, be used to interact an 803 nm wavelength pump pulse, having 90mJ of energy, and a 20 psec FWHM pulse duration, and, by Stimulated Raman Back-Scattering, amplify, and temporally compress, a counter propagating 878 nm wavelength seed pulse, initially having 16 μJ of energy and a 550 fsec FWHM pulse duration, to produce an 878 nm output pulse having about 3mJ of energy and a 90 fs FWHM pulse duration. As the seed pulse itself may have originated as a first Stoke beam from an 803 nm wavelength Ti:Sapphire laser beam having an initial intensity of $1.3 \times 10^{12}$ W/cm$^2$, the total intensity amplification of such a system may be about 10,000, providing an output pulse intensity of about $1.3 \times 10^{16}$ W/cm$^2$ on a 15 µm diameter spot size in the pulse duration of 90 fsec.

Such an output pulse, when focused down to an appropriate focal volume may provide a power density greater than $10^{12}$ Watts/cm$^2$ which may be sufficient to initiate highly localized, molecule disrupting processes, as described in more detail in, for instance, patents U.S. Pat. No. 8,187,256 issued on May 29, 2012, and U.S. Pat. No. 9,351,794 issued on May 31, 2016, the contents of both of which are hereby incorporated by reference in their entirety.

Figure 2A:
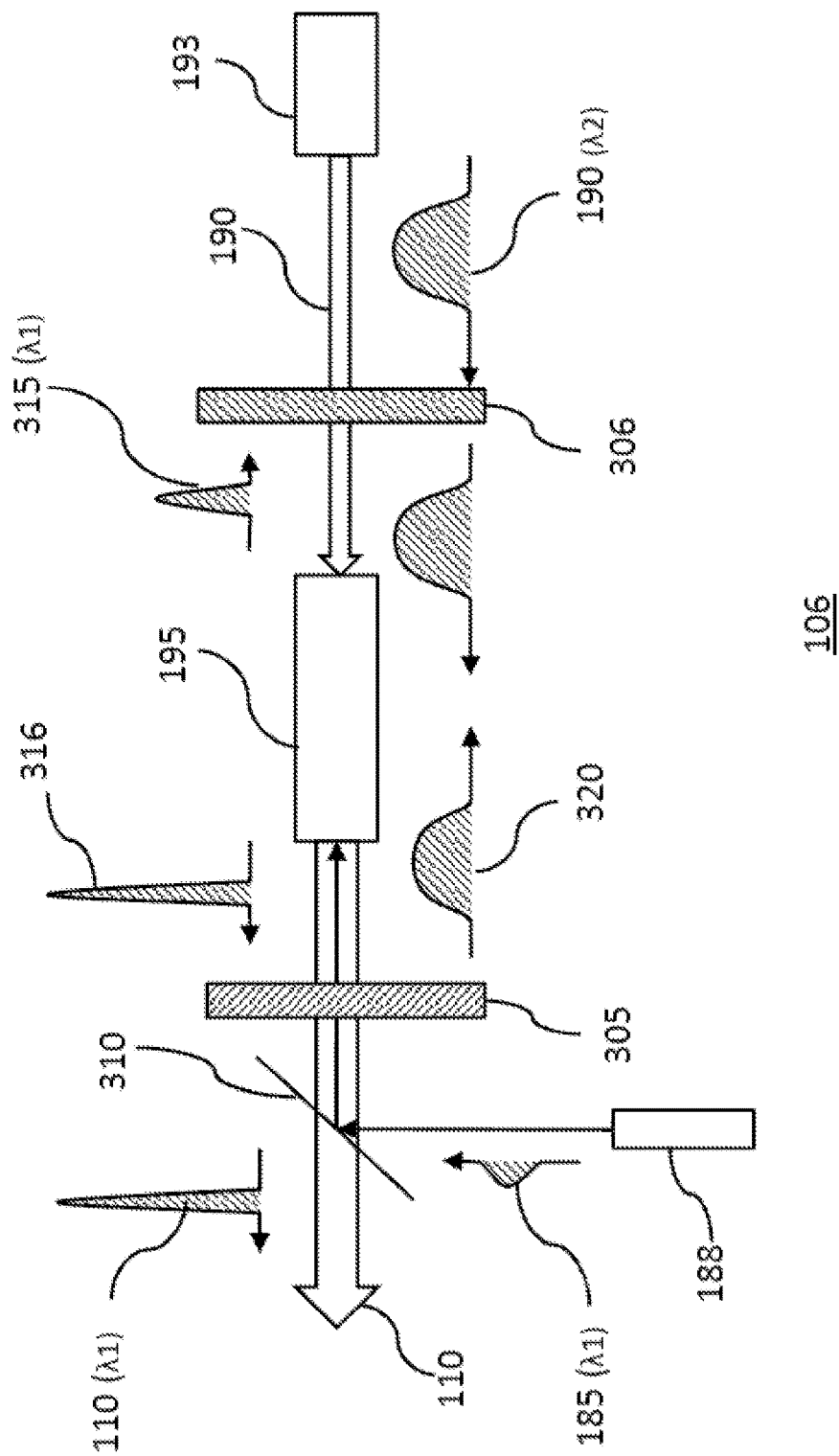
FIG. 2A shows a schematic representation of a double, or multi-pass Compact-Plasma Ultraintense Laser (mpC-PUL) of one example of an aspect of the present invention.

FIG. 2A shows a schematic representation of a double-pass, multi-pass Compact-Plasma Ultraintense Laser (mpC-PUL) of one example of an aspect of the present invention.

In the mpC-PUL 106 both the seed pulse 185(λ1) and the pump pulse 190(λ2) may be made to pass through the columnar plasma 195 twice by using two dichroic mirrors.

The 1st wavelength selective mirror 305 may, for instance, be chosen so as to transmit light at the wavelength of the seed pulse 185 while it is reflective at the wavelength of the pump pulse 190. Conversely, the 2nd wavelength selective mirror 306 may be chosen to be transmitting at the wavelength of the pump pulse 190 while it is reflecting at the wavelength of the seed pulse 185.

In this way, the pump pulse 190 emitted from the pump pulse laser 193 may pass through the 2nd wavelength selective mirror 306 and into the columnar plasma 195. At the same time, the seed pulse 185 from the seed pulse laser 188 may be placed on the lasing axis by a beam splitter having saturable absorber 310, and then pass through the 1st wavelength selective mirror 305 into the columnar plasma 195. In the columnar plasma 195, the seed pulse 185 may interact with the pump pulse 190 and be amplified and compressed by Stimulated Raman Back-Scattering, resulting in a one-pass amplified and compressed seed pulse 315.

The slightly depleted pump pulse 320 may then be reflected by the 1st wavelength selective mirror 305 and pass back through the columnar plasma 195. At the same time, the one-pass amplified and compressed seed pulse 315 may be reflected back by the 2nd wavelength selective mirror 306.

The one-pass amplified and compressed seed pulse 315 may then be coupled to the reflected, slightly depleted pump pulse 320 via a suitable plasma wave in the columnar plasma 195 and be further amplified and compressed by Stimulated Raman Back-Scattering to produce a two-pass amplified and compressed seed pulse 316. This two-pass amplified and compressed seed pulse 316 may now pass through the 1st wavelength selective mirror 305. The two-pass amplified and compressed seed pulse 316 may also pass through the beam splitter with saturable absorber 310 as the intensity of the pulse may now be several hundred times more intense than the seed pulse 185 that the beam splitter previously reflected. The two-pass amplified and compressed seed pulse 316 may then emerge as the output plasma laser pulse 110(λ1).

The need for a double pass Stimulated Raman Back-Scattering laser stems from the fact that in addition to amplification, there is a competing process of Landau damping of electro-magnetic (EM) waves in the plasma. This occurs because the plasma temperature increases due to the uninterrupted pump-heating of the plasma. This Landau damping process diminishes the amplification over time and distance of EM wave propagation in plasma. It is not, therefore, possible to simply double the length of the plasma column to obtain additional gain as may be done in most conventional lasing mediums. The double pass system introduces enough of a temporal delay of the pumping that the plasma may cool down, decreasing the Landau damping. A second pass through the slightly cooled plasma may, therefore, result in further increases in amplification, and further compression, of the pulses. More complex mirror arrangements may allow for an even higher number of effective passes.

The higher amplification of the multi-pass system may have the advantage that a less powerful, and therefore less expensive, system driving laser may be used to obtain the same intensity of final output pulse. This may, for instance, provide for more compact and affordable ultraintense and ultrashort pulse laser systems, allowing wider medical application of such systems.

Figure 2B:
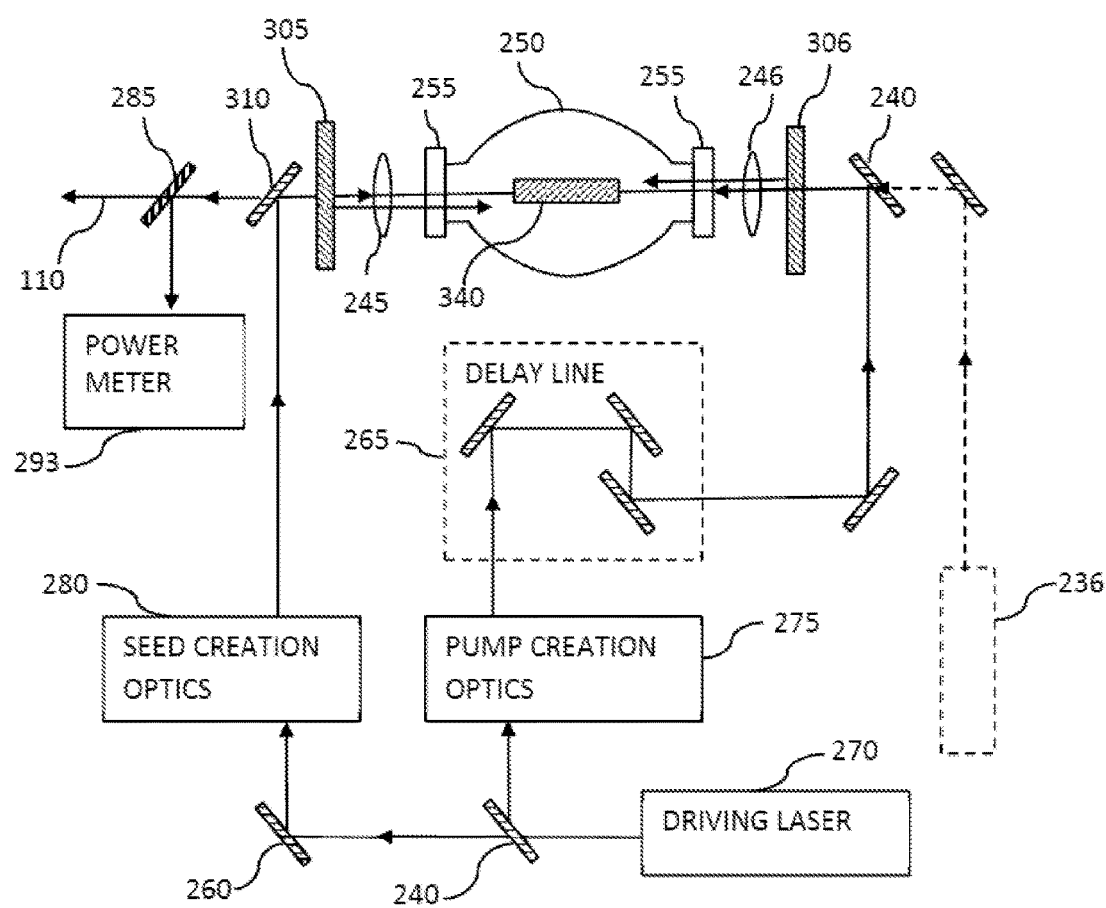
FIG. 2B shows a schematic representation of some significant components of a double, or multi-pass Compact-Plasma Ultraintense Laser (mpC-PUL) of one example of an aspect of the present invention.

FIG. 2B shows a schematic representation of some significant components of a double, or multi-pass Compact-Plasma Ultraintense Laser (mpC-PUL) of one example of an aspect of the present invention.

The amplifying-and-compressing medium may be a cylindrical plasma such as, but not limited to, an high voltage (HV) discharge plasma 340 contained inside an open ended plastic microcapillary. The microcapillary may be placed inside a vacuum chamber 250 that may be evacuated to a pressure of a few mill-Torr by a suitable low or non-vibrating vacuum pump such as, but not limited to, a sorption pump or a cryogenic pump or some combination thereof.

The plasma may be created by ablation of the plastic microcapillary wall using a pre-pulse from the driving laser 270, or it may be created by ionization of a gas injected into the microcapillary from a gas jet.

Creation of the plasma may also be done using a pre-pulse from the driving laser 270 or from an optional separate pre-pulse laser 236.

A pulse from the driving laser 270 may be split into two parts by a beam splitter 240, with the larger portion, typically 95%, being fed to the pump creation optics 275 where the pulse may be shaped by, for instance, being compressed. The pump pulse may then enter a delay line 265 before being fed on via a wavelength selective beam splitter 240 to be on the optical axis of the microcapillary containing the plasma, which may be a HV discharge plasma 340. The delay line 265, which may be an optical delay line may be used to control a delay between a pre-pulse and the pump pulse. In this way, the delay line 265 may be used to effectively control the initial plasma temperature during the second pass or, more generally, the initial temperatures in each following pass.

The smaller part of the driving laser 270, typically 5%, may be fed via one or more steering mirrors 260 into the seed creation optics 280. The seed creation optics 280 may both generate a Stokes beam having the requisite wavelength difference from the pump pulse to facilitate Stimulated Raman Back-Scattering in the plasma. The seed creation optics 280 may also compress this pulse by, for instance, using a paired grating compressor, to undo any dispersion of the pulse introduced by the crystal used for generating the Stokes beam. Once the seed pulse has been created, it may be fed onto the optical axis of the plasma being contained in the microcapillary by a beam splitter with a saturable absorber 310. The saturable absorber may allow the low intensity seed pulse to be reflected, but will become transparent to the more intense, amplified output laser pulse 110, allowing it to exit the system along the amplification axis.

The seed pulse may then pass through the 1st wavelength selective mirror 305, which may be a dichroic mirror constructed to be transmitting at the seed pulse wavelength, but reflecting at the wavelength of the pump pulse. A 1st focusing optical system 245 may then focus the seed pulse through a vacuum chamber optical window 255 and into the plasma column 340, which may be a HV discharge plasma.

Meanwhile, the pump pulse may have been focused by a 2nd focusing optical system 246 through a vacuum chamber optical window 255 into the plasma column 340.

The seed pulse and the pump pulse may then counter-propagate through the plasma column 340, amplifying and compressing the seed pulse by using Stimulated Raman Back-Scattering. When the amplified and compressed seed pulse reaches the 2nd wavelength selective mirror 306, it may be reflected back into the plasma column 340. Similarly, when the slightly depleted pump pulse reaches the 1st wavelength selective mirror 305, it may be reflected back into the plasma column 340. In this manner the once amplified and compressed seed pulse, and the slightly depleted pump pulse, may counter-propagate through a plasma that has had a brief, but sufficient, time to relax back to a distribution state that once again allows the seed pulse to be amplified and compressed by Stimulated Raman Back-Scattering. A beam splitter 285 may send a part of what is now the output laser pulse 110 to a power meter 293. This power meter 293 may, for instance, be used to monitor the operation of the laser, providing feedback for use in controlling, for instance, the power of the driving laser 270 and the delay in the delay line 265. The power meter may include a spectrometer and a charge-coupled device (CCD) that may be calibrated for measuring intensity as a function of wavelength.

A multi-pass Compact-Plasma Ultraintense Pulse Laser (mpC-PUL) 106 may require precise alignment of the pulses along the microcapillary axis. This may, for instance, be achieved by using a pointer laser, such as, but not limited to, a Helium Neon laser, as a reference beam to fix the position of the axis and so help align the various optical components.

In one exemplary demonstration of such a system, a 2 mm long, 50 μm diameter, columnar ethane plasma was created using a 6 nsec duration, 1064 nm wavelength pre-pulse having 600mJ of energy supplied by a Nd:YAG laser. This plasma was then used to interact an 803 nm wavelength pump pulse, having 90mJ of energy, and a 20 psec FWHM pulse duration with a counter propagating 878 nm wavelength seed pulse, initially having 16 μJ of energy and a 550 fsec FWHM pulse duration. In two, synchronized passes through the plasma, Stimulated Raman Back-Scattering amplification and compression, produced an 878 nm output pulse having almost 6mJ of energy and a 50 fs FWHM pulse duration. As the seed pulse itself may have originated as a first Stoke beam from an 80 nm wavelength Ti:Sapphire, the peak pulse intensity amplification of such a system may be about 20,000.

In this instance, the 2nd wavelength selective mirror 306 was a dichroic mirror having high reflectivity at 878 nm and high transmission at 803 nm and 1064 nm, while the 1st wavelength selective mirror 305 had high reflectivity at 803 nm and high transmission at both 878 nm and 1064 nm. The temporal delay between the pump pulse and the seed pulse was adjusted using the delay line 265 for the first pulse, and by the position along the lasing axis of the 1st wavelength selective mirror 305 for the second amplification pass.

Other optical components and their positioning may be used to obtain similar results. For instance, the plasma may be a plasma that results from ionizing any suitable gas that may be supplied by a gas jet such as, but not limited to, Hydrogen, Ethane or Nitrogen, or some combination thereof.

Similarly, other wavelength lasers may be used with other plasma electron densities. The Stimulated Raman Back-Scattering amplification condition $\omega_p = \omega_{pump} - \omega_{seed}$, where $\omega_p$ is the plasma frequency, $\omega_{pump}$ is the pump laser frequency and $\omega_{seed}$ is the seed laser pulse frequency, may, for instance, be satisfied by having a pump pulse wavelength $\lambda_{pump}$ of 532 nm (i.e. $\omega_{pump} = 3.54 \times 10^{15}$ radians/sec), a seed pulse wavelength $\lambda_{seed}$ of 566.5 nm (i.e. $\omega_{seed} = 3.33 \times 10^{15}$ radians/sec) which may be coupled by a plasma having $\omega_p = 0.21 \times 10^{15}$ radians/sec, corresponding to a plasma having an electron density of $n_e = 1.3 \times 10^{19}$ cm$^{-3}$.

These wavelengths may, for instance, be achieved using a 600mJ per pulse Nd:YAG laser, having an initial pulse duration of 3-5 nsec. A pump pulse of 30 psec duration and 200mJ energy could be obtained from such a laser. A small fraction, about 5%, of such a pump pulse could be split off and used to form a synchronized, longer wavelength seed pulse, compressed down to 0.5 psec. The 532 nm wavelength is the second harmonic of the fundamental wavelength 1064 nm of a Nd:YAG laser; in this sense the 532 nm wavelength is generated by Nd:YAG laser. A suitable non-linear optical crystal is used to double the frequency of the Nd:YAG laser, to obtain the 532 nm wavelength light from the 1064 nm wavelength light.

Figure 3:
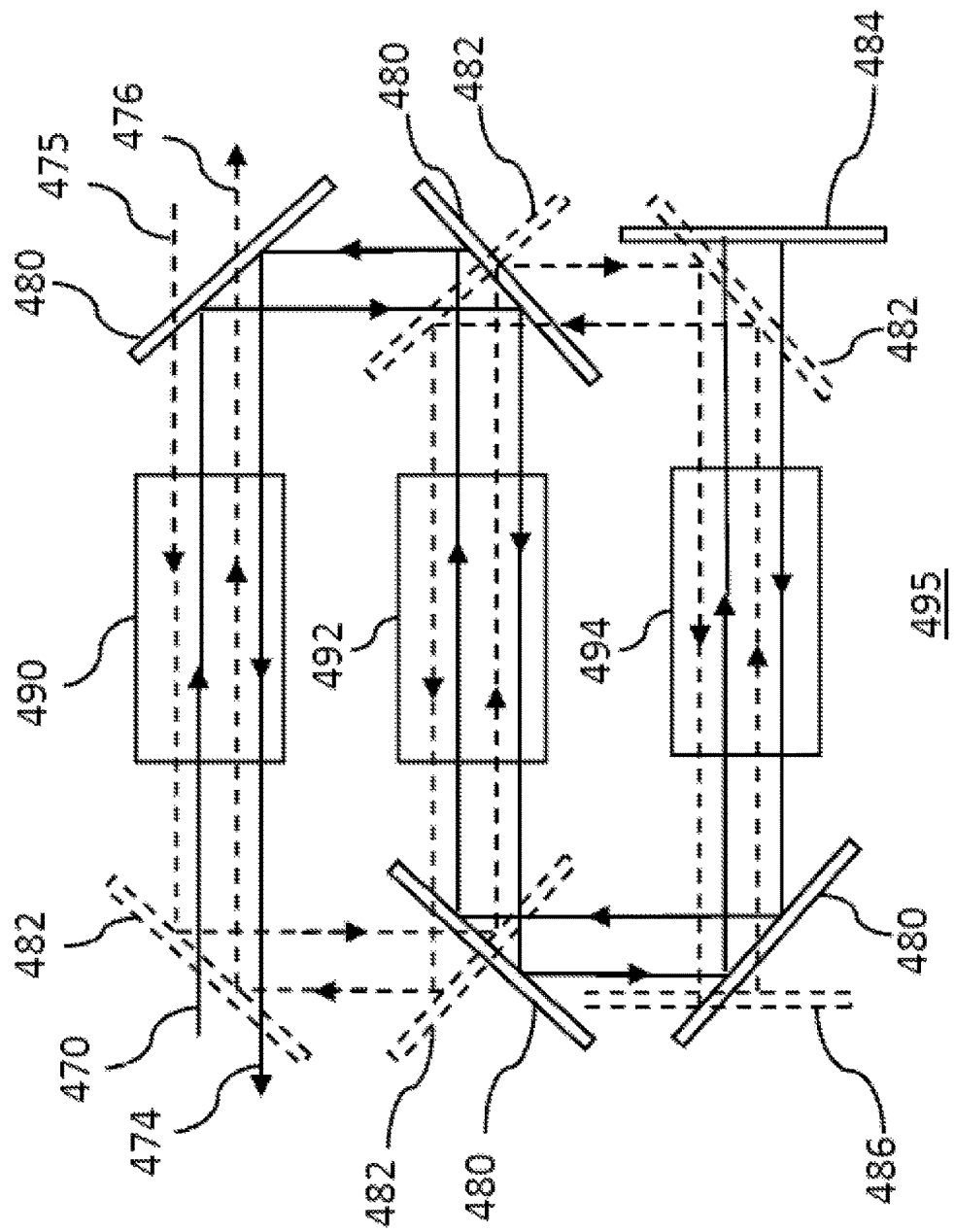
FIG. 3 shows a schematic representation of an arrangement of some relevant components of a six-pass, multi-pass, Compact-Plasma Ultraintense Laser (mpC-PUL) of one example of an aspect of the present invention.

FIG. 3 shows a schematic representation of a six-pass, multi-pass, Compact-Plasma Ultraintense Laser (mpC-PUL) 495 of one example of an aspect of the present invention.

The schematic representation of an optical arrangement for the six-pass, multi-pass, Compact-Plasma Ultraintense Laser (mpC-PUL) 495 shown in FIG. 3 may include three plasma columns, namely a first plasma region 490, a second plasma region 492 and a third plasma region 494. Each of these plasma regions, or plasma columns, may be oriented substantially parallel to each other.

The 6×-mpC-PUL 495 shown in FIG. 3 may also include four of a first type of dichroic mirror 480 that is highly reflective to a first wavelength of light incident at an acute angle, but significantly transparent to a second wavelength of light; four of a second type of dichroic mirror 482 that is significantly transparent to a first wavelength of light, but is highly reflective to a second wavelength of light incident at an acute angle; and one mirror 484 that retro-reflects a first wavelength of light and one mirror 486 that retro-reflects a second wavelength of light.

As shown in FIG. 3, the mirrors of the 6×-mpC-PUL may be arranged such that an incoming seed pulse 470, having a first wavelength, may be directed through one of the second type of dichroic mirror 482 and then on through the first plasma region 490 before being deflected down and then into the second plasma region 492 by a pair of the first type of dichroic mirror 480. The seed pulse may then continue on to be turned into the third plasma region 494, before being retro-reflected by the mirror 484 that retro-reflects a first wavelength of light. After that the seed pulse may then propagate back through the three plasma columns, or plasma regions, before emerging as output pulse 474.

At the same time, the incoming pump pulse 475, having a second wavelength, may travel on a path through the three plasma columns, being transmitted, deflected or retro-reflected by the dichroic mirrors such that it simultaneously counter-propagates twice with respect to the seed pulse in each of the plasma columns. In this way, as long the Raman Backscatter conditions are met, i.e., the wavelengths of the seed pulse and pump pulse, and the temperature of the plasma are such that the seed pulse frequency, $\omega_{seed}$, the pump pulse frequency $\omega_{pump}$, and the plasma columns' plasma frequency, $\omega_p$ satisfy the condition $\omega_p = \omega_{pump} - \omega_{seed}$ the seed pulse may be amplified and compressed on six occasions before it emerges as the output laser pulse 474.

One of ordinary skill in the art will appreciate that, although such an arrangement may require careful alignment and positioning of optical elements, it may, in principle, be adapted to use any number of plasma columns, and may result in 2n-times amplification and compression of the seed pulse, where n is the number of plasma columns used.

Figure 4:
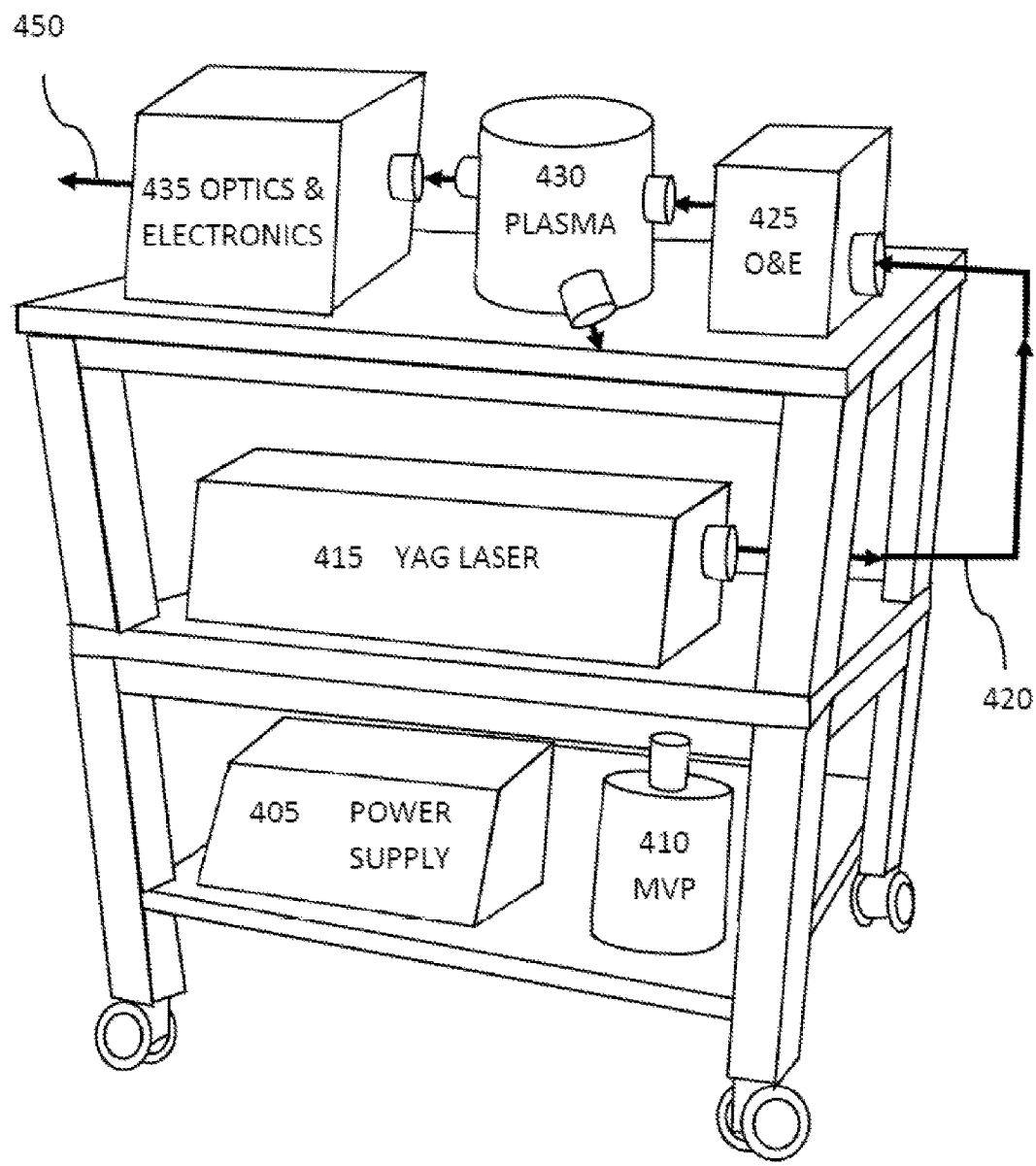
FIG. 4 shows a schematic representation of some significant components of a Compact-Plasma Ultraintense Laser (C-PUL) of one example of an aspect of the present invention.

FIG. 4 shows a schematic representation of some significant components of a Compact-Plasma Ultraintense Laser (C-PUL) of one example of an aspect of the present invention.

The relevant components of the C-PUL may, for instance, be arranged on a small optical cart and may include a small YAG pump laser 415, a power supply 405, a mechanical vacuum pump 410, optics and electronics 435 for the seed pulse and the output pulse, a vacuum chamber containing the gas jet 430 and optics and electronics 435 for the seed pulse and the output pulse.

The mechanical vacuum pump 410 may, for instance, be a pump such as the Becker VT series, rotary vane, oil-less vacuum pump as supplied by Becker Pumps Corporation of Cuyahoga Falls, Ohio Such a pump may, for instance, evacuate the vacuum chamber 430 down to a sufficiently low pressure to facilitate plasma column creation using gas jets.

As shown in FIG. 4, the pulses from the small YAG pump laser 415 may be transmitted to the optics and electronics 425 for the pre-pulse and pump-pulse and the optics and electronics 435 for the seed pulse and the output pulse via one or more fiber optic transfer links 420.

Figure 5:
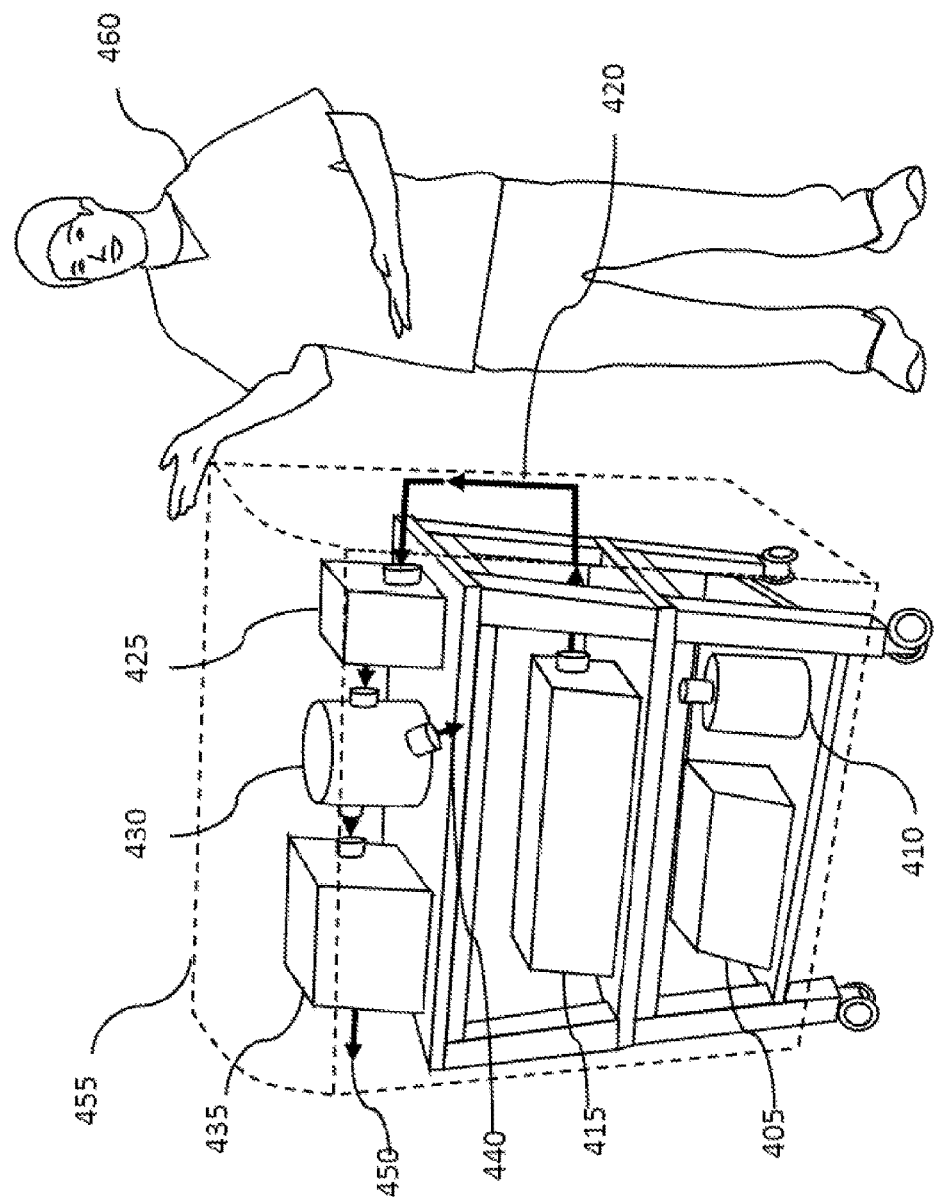
FIG. 5 shows a schematic representation of some significant components of a Compact-Plasma Ultraintense Laser (C-PUL) of one example of an aspect of the present invention, in a context of a dermatology use.

FIG. 5 shows a schematic representation of some significant components of a Compact-Plasma Ultraintense Laser (C-PUL) of one example of an aspect of the present invention in a context of a dermatological use.

In FIG. 5, the small YAG pump laser 415, the power supply 405, the mechanical vacuum pump 410, the optics and electronics 435 for the seed pulse and the output pulse, the vacuum chamber containing the gas jet 430, and the optics and electronics 435 for the seed pulse and the output pulse, are shown arranged on a mobile optical table and enclosed within a commercial, aesthetically pleasing housing 455. The unit is shown being attended by a schematic depiction of an average height attendant technician 460 so as to provide an indication of the scale of the equipment.

Although aspects of this invention have been described with a certain degree of particularity, it is to be understood that the present disclosure has been made only by way of illustration and that numerous changes in the details of construction and arrangement of parts may be resorted to without departing from the spirit and the scope of the invention.

In an example, there is provided a method for producing ultraintense laser pulses in which Stimulated Raman Back-Scattering (SRBS) amplifies and compresses a seed pulse, as well as an inventive compact plasma device, which may implement the method. SRBS is achieved by counter-propagating the seed pulse and a pump pulse through a few millimeter-long plasma having a plasma frequency equal to the difference between the pump and the seed pulse frequencies. Dichroic mirrors are arranged to provide two amplifying and compression passes through the plasma, allowing greater seed pulse amplification by mitigating Landau damping within the plasma that would occur in a single pass of a plasma of double the length. Alternate examples provide for 2n number of amplification and compression passes by providing n short plasma columns, where and additional, appropriately arranged dichroic mirrors. The compact size of the device, and the ultraintense, ultrashort pulses it emits, suit the device to dermatological applications, or to ophthalmic applications.

Examples of Dermatological Conditions Addressed

Currently, there are lasers that have US FDA (US Food and Drug Administration) approval to treat a variety of vascular lesions including superficial vascular malformations (port-wine stains), facial telangiectases, rosacea related erythema/redness, hemangiomas, pyogenic granulomas, Kaposi sarcoma and poikiloderma of Civatte.

Pigmented lesions that are treated include lentiginous regions and birthmarks including some congenital melanocytic naevi, blue naevi, naevi of Ota/Ito, and Becker naevi. These systems treat the lesions by confining their energy to the melanosomes, which are the tiny granules containing melanin inside the pigment cells and other skin cells.

Lasers are also be used to remove excessive and cosmetically undesired hair due to hypertrichosis or hirsutism.

Lasers may also be used to disable or reduce the effectiveness of an eccrine gland in order to decrease perspiration in an individual with excess sweating or hyperhidrosis. A very high intensity and very well localized laser beam interacting with tissue can be very effective for treatment the excess sweating or hyperhidrosis.

Facial wrinkles, acne scars and sun-damaged skin have also been treated with lasers, but the side effects of treatment typically include post-operative tenderness, redness, swelling and scarring. The redness and tenderness may last several weeks, while new skin grows over the area where the damaged skin has been removed by the laser treatments. Bacterial, fungal and viral skin infections, including reactivation of herpes virus, are also potential complications of current laser therapy until healing occurs. Extreme caution is needed when treating darker skinned individuals as permanent loss or variable pigmentation may occur long term. Keloids and hypertrophic scars are difficult to eradicate and traditional treatments are not always successful.

The multiphoton approach enabled by the apparatus and methods disclosed herein may address any or all these issues. However, it may be able to do this with a significant reduction in the pain, swelling, or scarring incurred by the process.

Moreover, the conditions may be addressed in a very short time span. For example, it has been shown that the removal of lentigenes may be addressed in a single session.

The multiphoton process appears to avoid any significant damage to the naturally occurring melanin in the skin.

The multiphoton process may, to a large extent, in practice, be independent of the wavelength of the laser light. This is in marked contrast to current methods that typically require matching a specific laser to a specific treatment. In the system and methods disclosed herein, a single laser type may be used to address a wide variety of dermatological conditions.

In an example, a location of a pigment on or within the patient is determined. The pigment may, for instance, be a tattoo pigment of an unwanted tattoo, or it may be some pigment of a blemish or a pigment associated with some unwanted growth such as, but not limited to, a carcinoma or a wart. A localized, multi-photon processing event is then initiated within a vicinity of the unwanted pigment in order to remove the pigment.

Figure 6:
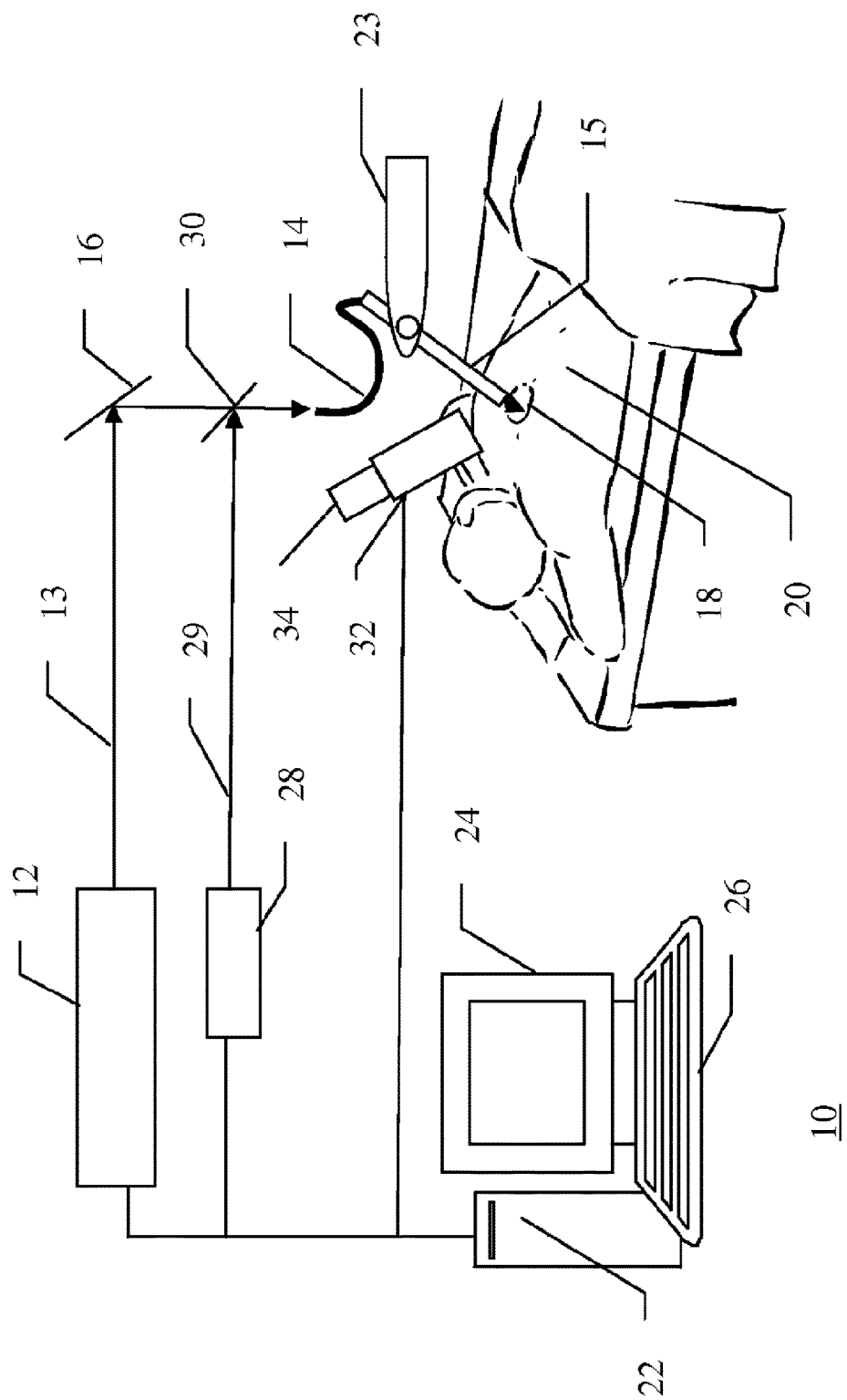
FIG. 6 shows a schematic drawing of an exemplary apparatus used for providing a multi-photon processing treatment.

A multi-photon processing treatment apparatus 10 may include a source of femtosecond laser pulses 12, such as one in which the femtosecond laser pulses are generated by Stimulated Raman Back-Scattering (SRBS) using a plasma gain-and-compression medium, such as one as described herein. The multi-photon processing treatment apparatus 10 may further include a fiber optic 14, a delivery optic 16, a delivery wand 15, a positioning unit 23, a control computer 22 having a viewing monitor 24 and an input device 26, a guidance light source 28, a mixing optic 30, a telescope 32 and a camera 34. The input device 26 may, for instance, be a keyboard, a touch screen, a mouse, a tablet or any other suitable computer input device. FIG. 6 shows a schematic drawing of an exemplary apparatus used for providing a multi-photon processing treatment.

NOTE

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

The invention claimed is:

1. Apparatus arranged to produce femtosecond laser pulses, the apparatus including a laser system arranged to produce nanosecond or picosecond laser pulses, an optical system configured to produce pump pulses and seed pulses from the nanosecond or picosecond laser pulses, and plasma generation apparatus including a vacuum chamber and plasma column generation apparatus arranged to generate a plasma column in the vacuum chamber, wherein the optical system is arranged to counterpropagate the pump pulses and the seed pulses along the plasma column, wherein the optical system is arranged to cause the pump pulses and the seed pulses to overlap in space and in time, in the plasma column, to amplify the seed pulses to produce amplified pulses, and to temporally shorten the amplified pulses compared to the seed pulses, to produce femtosecond amplified and shortened pulses, using stimulated Raman backscattering (SRBS) in the plasma column.

2. The apparatus of claim 1, wherein the femtosecond amplified and shortened pulses have a pulse energy in the range of 0.5 mJ to 200 mJ.

3. The apparatus of claim 2, wherein the femtosecond amplified and shortened pulses have a pulse energy in the range of 1 mJ to 40 mJ.

4. The apparatus of claim 3, wherein the femtosecond amplified and shortened pulses have a pulse energy in the range of 2 mJ to 15 mJ.

5. The apparatus of claim 1, wherein the femtosecond amplified and shortened pulses have a pulse FWHM (full width half maximum) duration below 500 fs.

6. The apparatus of claim 5, wherein the femtosecond amplified and shortened pulses have a pulse FWHM (full width half maximum) duration of 100 fs or less.

7. The apparatus of claim 5, wherein the femtosecond amplified and shortened pulses have a pulse FWHM (full width half maximum) duration of from 30 fs to 100 fs.

8. The apparatus of claim 1, wherein the plasma column is less than 3.0 cm in length, e.g. less than 1.0 cm in length.

9. The apparatus of claim 1, wherein the plasma column is less than 3 mm in length.

10. The apparatus of claim 1, wherein the plasma column is less than 100 µm in diameter.

11. The apparatus of claim 1, wherein the apparatus is less expensive than a Ti:sapphire laser system with equivalent laser pulse output.

12. The apparatus of claim 1, wherein the optical system is arranged such that after a first pass of the plasma column, a second pass of the plasma column by the laser pulses is provided, to provide femtosecond further amplified and further shortened pulses, by further stimulated Raman backscattering (SRBS) in the plasma column, in the second pass of the plasma column.

13. The apparatus of claim 1, in which the plasma column generation apparatus is arranged to generate one or more additional plasma columns in the vacuum chamber, wherein the optical system is arranged to counterpropagate the pump pulses and the femtosecond amplified and shortened pulses along the one or more additional plasma columns, wherein the optical system is arranged to cause the pump pulses and the femtosecond amplified and shortened pulses to overlap in space and in time, in the one or more additional plasma columns, to further amplify the femtosecond amplified and shortened pulses to produce further amplified pulses, and to temporally shorten the further amplified pulses, to produce femtosecond further amplified and shortened pulses, using stimulated Raman backscattering (SRBS) in each of the one or more additional plasma columns.

14. The apparatus of claim 1, wherein the plasma column generation apparatus comprises a laser for laser ablation, arranged to perform laser ablation of a suitable material.

15. The apparatus of claim 14, wherein the suitable material includes an open ended plastic microcapillary.

16. The apparatus of claim 1, wherein the plasma column generation apparatus comprises a gas jet and a high voltage apparatus arranged to perform high voltage ionization of the gas jet.

17. The apparatus of claim 16, wherein the plasma column generation apparatus includes a gas nozzle within the vacuum chamber, arranged to emit the gas jet.

18. The apparatus of claim 17, wherein the gas jet is injected into a plastic microcapillary, in which the gas jet injected into the plastic microcapillary is ionized in the plastic microcapillary.

19. The apparatus of claim 17, wherein the gas jet is a gas jet of Hydrogen ($H_2$), Nitrogen ($N_2$), or Ethane ($C_2H_6$), or some combination thereof.

20. The apparatus of claim 1, wherein the apparatus is mobile.

21. The apparatus of claim 20, the apparatus including a cart, the cart supporting the laser system, the optical system, and the plasma generation apparatus, wherein the cart is operable to transport the laser system, the optical system, and the plasma generation apparatus.

22. Method of using an apparatus arranged to produce femtosecond laser pulses, the apparatus including a laser system arranged to produce nanosecond or picosecond laser pulses, an optical system configured to produce pump pulses and seed pulses from the nanosecond or picosecond laser pulses, and plasma generation apparatus including a vacuum chamber and plasma column generation apparatus arranged to generate a plasma column in the vacuum chamber, wherein the optical system is arranged to counterpropagate the pump pulses and the seed pulses along the plasma column, wherein the optical system is arranged to cause the pump pulses and the seed pulses to overlap in space and in time, in the plasma column, to amplify the seed pulses to produce amplified pulses, and to temporally shorten the amplified pulses compared to the seed pulses, to produce femtosecond amplified and shortened pulses, using stimulated Raman backscattering (SRBS) in the plasma column, the method including the step of using the apparatus for dermatological treatment.

23. The method of claim 22, wherein the dermatological treatment is non-therapeutic.

24. The method of claim 22, wherein the dermatological treatment includes tattoo removal.

25. The method of claim 22, wherein the dermatological treatment includes treatment of superficial vascular malformations (port-wine stains), or facial telangiectases, or rosacea related erythema/redness, or hemangiomas, or pyogenic granulomas, or Kaposi sarcoma, or poikiloderma of Civatte, or lentiginous regions, or birthmarks, or facial wrinkles, or acne scars, or sun-damaged skin.

26. The method of claim 22, wherein the dermatological treatment includes use of multi-photon ablation.

27. A method for providing a compact laser having ultrashort and ultraintense output pulses, comprising:
providing a seed optical pulse having a seed wavelength, $\lambda_{seed}$, with a frequency $\omega_{seed}$,
providing a pump optical pulse having a pump wavelength, $\lambda_{pump}$ with a frequency $\omega_{pump}$;
providing a first plasma column having a plasma frequency, $\omega_p$ and wherein said plasma frequency, said seed frequency, and said pump frequency satisfy the condition that:

$\omega_p = \omega_{pump} - \omega_{seed}$;

propagating said seed optical pulse through said first plasma column in a first direction; and
simultaneously propagating said pump optical pulse through said first plasma column in a second, opposite direction such that said counter-propagating seed optical pulse and pump optical pulse are coupled by said first plasma column to produce Stimulated Raman Back-Scattering such that said seed optical pulse is amplified, and shortened in temporal length.

28. The method of claim 27, further comprising:
providing a beam splitter comprising a saturable absorber;
providing a 1st wavelength selective mirror being transmitting at said seed wavelength, $\lambda_{seed}$, and reflective at said pump wavelength, $\lambda_{pump}$ and located between said beam splitter and said plasma column;
providing a 2nd wavelength selective mirror being transmitting at said pump wavelength, $\lambda_{pump}$, and reflective at said seed wavelength, $\lambda_{seed}$ and located on an opposite side of said plasma column to said beam splitter;
using said beam splitter to propagate said seed optical pulse through said 1st wavelength selective mirror and then through said plasma column, while simultaneously counter-propagating said pump optical pulse through said 2nd wavelength selective mirror and then through said plasma column; and
then, reflecting said pump optical pulse from said 1st wavelength selective mirror back through said plasma column, while simultaneously reflecting said seed optical pulse from said 2nd wavelength selective mirror, through said plasma column, then through said 1st wavelength selective mirror, then through said beam splitter comprising a saturable absorber, thereby producing a twice amplified and compressed seed optical pulse as an output laser pulse.

29. The method of claim 28, wherein said seed optical pulse has a seed optical pulse energy of less than 100 µJ and a seed optical pulse width of less than 1 psec; and said pump optical pulse having a pump optical pulse energy of less than 200mJ and a pump optical pulse width of less than 50 psec, and wherein said output laser pulse has a pulse width less than 300 fsec.

30. The method of claim 29, wherein said plasma column has a length shorter than 5 mm.

31. The method of claim 30, wherein said plasma column is one of a hydrogen plasma, an ethane plasma and a nitrogen plasma, or some combination thereof.

32. The method of claim 30, wherein said plasma column is an ethane plasma.

33. The method of claim 31, wherein said pump optical pulse has a wavelength of 532 nm, said seed optical pulse has a wavelength of 566.5 nm and said plasma has an electron density of $1.3 \times 10^{19}$ electrons/cm$^3$.

34. The method of claim 30, including a step of using a cylindrical microcapillary tube having an internal diameter of less than 500 µm, a length less than 10 mm and an initial, internal gas pressure of less than 100 Torr and wherein said plasma column is contained within said microcapillary tube.

35. The method of claim 34, the microcapillary tube further comprising a polyethane tube, wherein formation of said plasma column is initiated by laser ablation of said polyethane tube.

36. The method of claim 28, further comprising:
a second plasma column oriented substantially parallel to said first plasma column;
a third and a fourth wavelength selective mirror being transmitting at said seed wavelength, $\lambda_{seed}$, and reflective at said pump wavelength, $\lambda_{pump}$;
a fifth and a sixth wavelength selective mirror being transmitting at said pump wavelength, $\lambda_{pump}$, and reflective at said seed wavelength, $\lambda_{seed}$; and
wherein, said six wavelength selective mirrors are positioned and oriented such that said seed optical pulse and said pump optical pulse simultaneously counter-propagate through said first plasma column, then simultaneously counter-propagate twice through said second plasma column, and then simultaneously counter-propagate through said first plasma column, thereby amplifying and compressing said seed optical pulse four times to produce said output laser pulse.

* * * * *